(12) United States Patent
Fujita et al.

(10) Patent No.: US 8,900,882 B2
(45) Date of Patent: Dec. 2, 2014

(54) METHOD OF ASSAYING COMPLEX AND KIT TO BE USED THEREFOR

(75) Inventors: Kiyotaka Fujita, Matsumoto (JP); Ryo Kojima, Koriyama (JP); Yoshiro Sato, Koriyama (JP); Natsuki Sato, Koriyama (JP)

(73) Assignees: Nitto Boseki Co., Ltd., Fukushima-Shi (JP); Shinshu University, Matsumoto-Shi (JP)

( * ) Notice: Subject to any disclaimer, the term of this patent is extended or adjusted under 35 U.S.C. 154(b) by 824 days.

(21) Appl. No.: 13/056,040

(22) PCT Filed: May 14, 2009

(86) PCT No.: PCT/JP2009/058973
§ 371 (c)(1),
(2), (4) Date: Feb. 25, 2011

(87) PCT Pub. No.: WO2010/013525
PCT Pub. Date: Feb. 4, 2010

(65) Prior Publication Data
US 2011/0136261 A1  Jun. 9, 2011

(30) Foreign Application Priority Data
Jul. 31, 2008 (JP) ................................ 2008-197156

(51) Int. Cl.
*G01N 33/543* (2006.01)
*G01N 33/536* (2006.01)

(52) U.S. Cl.
CPC ........ *G01N 33/536* (2013.01); *G01N 2333/765* (2013.01)
USPC .......... 436/518; 435/7.1; 435/7.92; 435/7.93; 436/501; 436/523

(58) Field of Classification Search
None
See application file for complete search history.

(56) References Cited

U.S. PATENT DOCUMENTS

| 5,278,080 | A  | * | 1/1994  | Midgley et al. | ............... | 436/500 |
| 5,391,479 | A  | * | 2/1995  | Bobrow         | ............... | 435/5   |
| 7,824,876 | B2 | * | 11/2010 | Qin et al.     | ............... | 435/7.4 |
| 2002/0127741 | A1 | * | 9/2002  | Sales et al. | ............... | 436/533 |
| 2004/0197842 | A1 | * | 10/2004 | Morrissey    | ............... | 435/7.92 |
| 2006/0172351 | A1 | * | 8/2006  | Sumida et al.| ............... | 435/7.23 |
| 2008/0096233 | A1 | * | 4/2008  | Robotti et al.| ............... | 435/7.23 |
| 2011/0257029 | A1 | * | 10/2011 | Haab et al.  | ............... | 506/9 |

FOREIGN PATENT DOCUMENTS

| JP | 2-114181 | 4/1990 |
| JP | 2-193071 | 7/1990 |
| JP | 5-207893 | 8/1993 |

OTHER PUBLICATIONS

Fujita et al., Identification and properties of glycated monoclonal IgA that affect the Fructosamine assay., Clinical Chemistry 49, No. 5, 2003, pp. 805-808.*
Piironen et al., Measurment orf Circulating Forms of Prostate-specific Antigen in Whole Blood Immediately after Venipuncture: Implications of Point-of-Care Testing, Clinical Chemistry 47:4, 2001, pp. 703-711.*
Jung et al., Determination of Alpha1-Antichymotrypsin-PSA Complex in Serum does not improve the differentiation between benign prostatic hyperplasia and prostate cancer compared with total PSA and percent free PSA, Urology 53 (6), 1999, pp. 1160-1167.*
Fujita K. et al., "Mechanism of IgA-albumin complex formation that affects the fructosamine assay", *J Electrophoresis*, 2006, vol. 50, p. 19-23.
Yamauchi M. et al., "Establishment of method for measuring IgA-albumin complex by Elisa assay and its problems", 54th Meeting of Japanese Society of Laboratory Medicine, Abstracts, Oct. 31, 2007, p. 133, O-006, English translation portions only.

* cited by examiner

*Primary Examiner* — Gary W Counts
(74) *Attorney, Agent, or Firm* — Kratz, Quintos & Hanson, LLP

(57) ABSTRACT

In the case of assaying the level of complex AB in a sample which likely contains the complex AB composed of substance A with another substance B, the complex is assayed by the competitive homogeneous assay method with the use of reagents including a reagent containing partner C specifically binding to substance A, a reagent containing partner D specifically binding to substance B, a reagent containing fine particles carrying substance A or an analog thereof and substance B or an analog thereof, and a reagent containing partner C specifically binding to substance A and partner D specifically binding to substance B. Thus, the complex in the sample can be easily assayed. The above method is applicable to general-purpose biochemical automatic analyzers.

7 Claims, 5 Drawing Sheets

IgA CONCENTRATION + ALBUMIN CONCENTRATION [mg/dL]

METHOD OF ASSAYING COMPLEX AND KIT TO BE USED THEREFOR

TECHNICAL FIELD

The present invention relates to a method of assaying a complex in a sample and a kit to be used therefor. More particularly, the present invention relates to a method of assaying a complex in a sample using a competitive homogeneous agglutination assay, wherein the method is suitable for assaying a complex of two different substances such as IgA-albumin complex present in a sample, and to a kit to be used therefor.

BACKGROUND ART

In blood samples, many substances are present in the form of a complex of two different substances. For such kinds of complexes, transferrin-transferrin receptor complex, thrombin-antithrombin complex, factor VIIa-antithrombin complex, oxidized LDL-CRP complex, PSA-α2-macroglobulin complex, PSA-antichymotrypsin complex, oxidized LDL-α1-antitrypsin complex, protein C inhibitor-protease complex, plasmin-α2-plasmin inhibitor complex, PSA-protein C inhibitor complex, plasminogen activator inhibitor-tissue plasminogen activator complex, haptoglobin-hemoglobin complex, transthyretin-retinol binding protein complex and the like are known.

As methods for identifying these complexes like a complex of substance A and substance B, or for assaying the levels thereof, the following examples are known. The first one is a method using an electrophoresis (Patent Literature 1). The second one is a method where the complex in a sample is determined by allowing the complex to get contact with a solid phase antibody made through binding either one of an antibody against substance A and an antibody against substance B to a solid phase, and simultaneously to react with a labeled antibody derived from the other antibody that is not immobilized to the solid phase (Patent Literature 2). The third one is a method of assaying the complex by various kinds of immunoassay using an antibody specific to the complex but with low affinity for the individual released components of the complex (Patent Literature 3). The first method, however, has a disadvantage that the sensitivity and quantitativeness are low and that the operation is complicated. The second method has a problem that a general-purpose automatic biochemical analyzer cannot be applied for the assay owing to the utilization of a solid phase, requiring much time in washing procedure, reaction and so on. In the third method, there has been a problem that it is difficult in some cases to obtain an antigen to be used for the production of an antibody against the complex or to obtain a specific antibody, and that it is also difficult to assay the complex accurately owing to a matter of specificity. Thus, in a homogeneous system, there is a need for the development of a simple method for assaying complexes, for which necessary reagents are readily available and which is applicable to automatic biochemical analyzers.

Meanwhile, it has recently been reported that an IgA-albumin complex was isolated from five patients with IgA-type M-proteinemia and that the complex was confirmed to be present by a Western Blot (Non Patent Literature 1), whereas no simple method of measuring its level is known.

CITATION LIST

Patent Literature

Patent Literature 1: JP 02-114181 A
Patent Literature 2: JP 02-193071 A
Patent Literature 3: JP 05-207893 A

Non Patent Literature

Non Patent Literature 1: Fujita et al, J Electrophoresis, vol. 50, p. 19, 2006

SUMMARY OF INVENTION

Technical Problem

Therefore, it is an object of the present invention to provide a simple method for assaying complexes, especially in a homogeneous system, for which necessary reagents are readily available and which is applicable to automatic biochemical analyzers, and a kit to be used therefor. It is another object of the invention to provide a simple method to assay the level of IgA-albumin complex.

Solution to Problem

Under such circumstances, to solve these problems, the present inventors conducted investigations to develop a simple method to assay the level of a complex of substance A and substance B such as IgA-albumin complex. As a result, the inventors have developed a latex reagent carrying two kinds of substances, and using this, the inventors have further discovered that the level of a complex of interest can be determined with an automatic analyzer, based on values obtained in three competitive homogeneous agglutination assays, which are carried out with combined usages of three kinds of reagents consisting of a reagent comprising a substance A-specific binding partner such as a substance A-specific antibody, a reagent comprising a substance B-specific binding partner such as a substance B-specific antibody, and a reagent comprising the substance A-specific binding partner and the substance B-specific binding partner. The inventors have also found that the level of IgA-albumin complex can be easily determined by this method. The present invention has been accomplished through such process.

More specifically, the present invention is a method of assaying the level of complex AB of substance A and substance B in a sample which is likely to contain complex AB, characterized by comprising:

i) determining level P, which is the level of substance A present in complex AB and in a free form in the sample, through the steps of mixing the sample, a substance A-specific binding partner C, and fine particles carrying substance A or an analogue thereof and substance B or an analogue thereof, in order to allow competition for a specific binding reaction with the specific binding partner C between substance A present in complex AB and in a free form in the sample and substance A or the analogue carried on the fine particles; and determining level P based on the degree of agglutination of the specific binding partner C with substance A or the analogue carried on the fine particles;

ii) determining level Q, which is the level of substance B present in complex AB and in a free form in the sample, through the steps of mixing the sample, a substance B-specific binding partner D, and the fine particles carrying substance A or the analogue and substance B or the analogue, in order to allow competition for a specific binding reaction with the specific binding partner D between substance B present in complex AB and in a free form in the sample and substance B or the analogue carried on the fine particles; and determining level Q based on the degree of agglutination of the specific binding partner D with substance B or the analogue carried on the fine particles;

iii) determining level R through the steps of: mixing the sample, the substance A-specific binding partner C, the substance B-specific binding partner D, and the fine particles carrying substance A or the analogue and substance B or the analogue, in order to allow competition for a specific binding reaction with the specific binding partner C between substance A present in complex AB and in a free form in the sample and substance A or the analogue carried on the fine particles as well as competition for a specific binding reaction with the specific binding partner D between substance B present in complex AB and in a free form in the sample and substance B or the analogue carried on the fine particles; and determining level R based on the sum of the degree of agglutination of the specific binding partner C with substance A or the analogue carried on the fine particles and the degree of agglutination of the specific binding partner D with substance B or the analogue carried on the fine particles; and iv) calculating level α of complex AB according to the formula α=P+Q−R.

Further, the present invention is a kit for assaying the level of complex AB of substance A and substance B in a sample, the kit comprising:

i) a reagent containing fine particles carrying substance A or an analogue thereof and substance B or an analogue thereof;

ii-A) a reagent containing a substance A-specific binding partner C;

ii-B) a reagent containing a substance B-specific binding partner D; and

II-C) a reagent containing the substance A-specific binding partner C and the substance B-specific binding partner D.

Further, the present invention is a method of assaying the level of complex AB of substance A and substance B in a sample which is likely to contain complex AB, characterized by comprising:

i) determining level P, which is the level of substance A present in complex AB and in a free form in the sample;

ii) determining level Q, which is the level of substance B present in complex AB and in a free form in the sample; and iii) determining level R through the steps of: mixing the sample, a substance A-specific binding partner C, a substance B-specific binding partner D, and fine particles carrying substance A or an analogue thereof and substance B or an analogue thereof, in order to allow competition for a specific binding reaction with the specific binding partner C between substance A present in complex AB and in a free form in the sample and substance A or the analogue carried on the fine particles as well as competition for a specific binding reaction with the specific binding partner D between substance B present in complex AB and in a free form in the sample and substance B or the analogue carried on the fine particles; and determining level R based on the sum of the degree of agglutination of the specific binding partner C with substance A or the analogue carried on the fine particles and the degree of agglutination of the specific binding partner D with substance B or the analogue carried on the fine particles; and iv) calculating level α of complex AB according to the formula α=P+Q−R.

Further, the present invention is a method of assaying IgA-albumin complex in a sample, characterized by an immunoassay using an antibody against IgA and an antibody against albumin.

Advantageous Effects of Invention

According to the method and the kit of the present invention, a complex in a sample can be assayed easily with the use of readily available reagents. In addition, this method and kit can be applied to a general-purpose automatic biochemical analyzer, and therefore a complex of interest can be assayed easily in multiple samples in a short time. Also, the level of IgA-albumin as a complex can be assayed easily.

DESCRIPTION OF EMBODIMENTS

Figure 1:
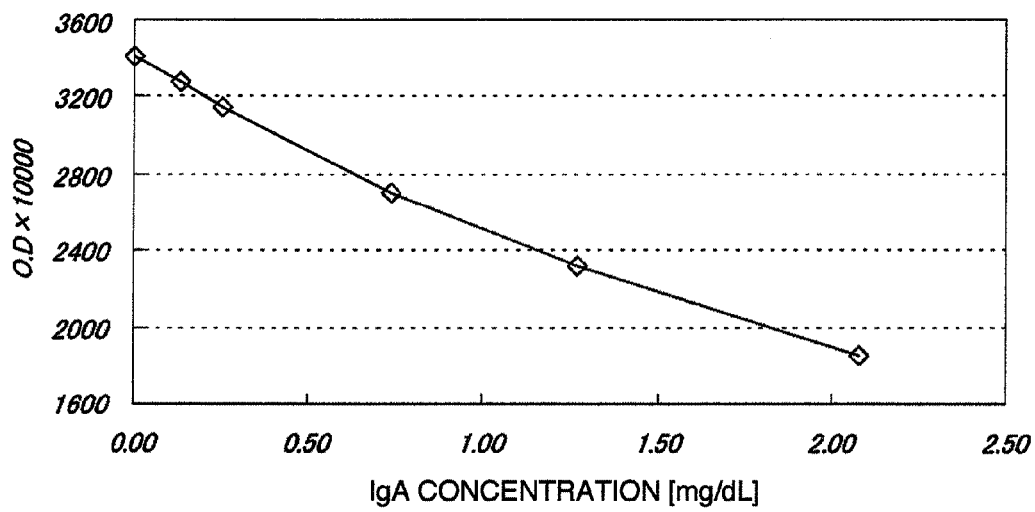
FIG. 1 shows the change of absorbance level when a standard sample was measured using a first reagent and a second reagent-A in Example 1.

To the present invention is applied the fact that a substance in a sample can be assayed based on a principle that in a competitive homogeneous agglutination assay such as a competitive homogeneous immunoagglutination assay, among the reagents used for the reaction and the reaction products, only one component has a turbidity while other components are dissolved in water.

As used herein, the competitive homogeneous immunoagglutination assay refers to a method for quantitatively determining the level of an antigen to be assayed through the steps of mixing a sample containing the antigen to be assayed, an antibody against the antigen, and fine particles carrying an antigen capable of binding to the antibody, in order to allow competition for an antigen-antibody reaction with the antibody between the antigen in the sample and the antigen carried on the fine particles; and quantitatively determining the level of the antigen to be assayed based on the degree of agglutination due to the antigen-antibody reaction between the antigen carried on the fine particles and the antibody.

As used herein, the competitive homogeneous agglutination assay refers to a method for quantitatively determining the level of a substance to be assayed through the steps of: mixing a sample containing the substance to be assayed, a specific binding partner for the substance, and fine particles carrying a substance capable of binding to the specific binding partner, in order to allow competition for a specific binding reaction with the specific binding partner between the substance in the sample and the substance carried on the fine particles; and quantitatively determining the level of the substance to be assayed based on the degree of agglutination due to the specific binding reaction between the substance carried on the fine particles and the specific binding partner.

The general principle of the competitive homogeneous agglutination assay will be illustrated below.

First, (i) a substance to be assayed in a sample; (ii) a conjugate of the same substance as that to be assayed or its analogue and fine particles as a reagent; and (iii) a specific binding partner for the substance to be assayed as a reagent are used as the sample and reagents to be mixed for the reaction. All of the substance and reagents (i) to (iii) are soluble in water or can be homogeneously dispersed in water. Then, these are mixed and subjected to a specific binding reaction such as antigen-antibody reaction, which causes a competitive formation of two specific binding reaction products: (iv) a binding product between the conjugate (ii) and the specific binding partner (iii); and (v) a binding product between the substance (i) and the specific binding partner (iii). The binding product (iv) is insoluble in water and causes turbidity, whereas the binding product (v) is soluble in water. Accordingly, the more binding product (iv) formed, the greater the turbidity of the reaction solution (the degree of agglutination).

In this competitive reaction, the substance (i) competes with the conjugate (ii) for the reaction with a limited amount of the specific binding partner (iii), and thereby the resultant insoluble binding product (iv) decreases in quantity and concomitantly the degree of turbidity in the reaction solution decreases. Therefore, the higher the concentration of the substance to be assayed in a sample, the lower the degree of turbidity of the reaction solution. Hence, it is possible to assay the level of the substance in a sample based on the degree of turbidity.

In the competitive homogeneous agglutination assay such as a competitive homogeneous immunoagglutination assay used in the present invention, since the calibration curve is a decay curve, there is an advantage that the prozone phenomenon that is a weak point of the homogeneous agglutination assay such as a usual immunoagglutination assay does not occur.

The method of the present invention to assay a complex is characterized, for example, by using "a conjugate as a reagent in which substance A or its analogue and substance B or its analogue are carried on fine particles" as "a conjugate of the same substance as that to be assayed or its analogue and fine particles as a reagent" that is the (ii) in the above mentioned theory. In the present invention, preferably the competitive homogeneous agglutination assay is carried out three times, and level P, which is the level of substance A present in complex AB and in a free form in the sample, level Q, which is the level of substance B present in complex AB and in a free form in the sample, and level R are determined. In this case, "a specific binding partner for substance A as a reagent", "a specific binding partner for substance B as a reagent" and "both of the specific binding partner for substance A and the specific binding partner for substance B as a reagent" are, respectively, used in the three assays as "a specific binding partner for the substance to be assayed as a reagent" that is the (iii) in the above mentioned theory, and the levels P, Q and R are determined based on the respective degree of agglutination. Finally, the level of complex AB in the sample can be measured by determining level $\alpha$ of complex AB according to the formula $\alpha = P + Q - R$.

Meanwhile, in the present invention, level P of substance A, and level Q of substance B may be determined by known methods. Examples of known methods may include turbidimetric immunoassay (TIA method) and latex turbidimetric immunoassay.

The present invention is a method of assaying the level of complex AB of substance A and substance B in a sample that is likely to contain complex AB.

In the present invention, complex AB is not particularly limited as long as it is a complex of two different substances, substance A and substance B. As a complex, for example, transferrin-transferrin receptor complex, thrombin-antithrombin complex, factor VIIa-antithrombin complex, oxidized LDL-CRP complex, PSA-$\alpha$2-macroglobulin complex, PSA-antichymotrypsin complex, oxidized LDL-$\alpha$1-antitrypsin complex, protein C inhibitor-protease complex, plasmin-$\alpha$2-plasmin inhibitor complex, PSA-protein C inhibitor complex, plasminogen activator inhibitor-tissue plasminogen activator complex, haptoglobin-hemoglobin complex, transthyretin-retinol binding protein complex, IgA-albumin complex and the like are preferred. In the present invention, either one or both of the two constituents of the complex, the substances A and B, may be present in the sample in a form different from the complex, for example, in a free uncombined form.

Samples are not limited as long as they are likely to contain complex AB, and may preferably be biological samples exemplified by plasma, serum and urine.

As used herein, the specific binding partner C for substance A, and the specific binding partner D for substance B, are not particularly limited, as long as they are, respectively, a binding partner capable of undergoing specific binding reaction with substance A present in complex AB and in a free form, and a binding partner capable of undergoing specific binding reaction with substance B present in complex AB and in a free form, and from the viewpoint of specificity and versatility, they may preferably be an antibody against substance A and an antibody against substance B, respectively. Such antibodies are those against the antigen, namely, the substance to be assayed, and so long as they are such antibodies, antisera, polyclonal antibodies or monoclonal antibodies may all be used.

When the substance is avidin, biotin, a hormone or a hormone receptor, the examples of the corresponding specific binding partners other than antibodies, may include biotin, avidin, a hormone receptor, or a hormone, etc.

As used herein, the "analogue" in "substance A or an analogue thereof" is not particularly limited so long as it is a substance capable of undergoing specific binding reaction with a specific binding partner for substance A and it is a substance other than substance A. The analogue is, in general, similar to substance A in structure. When substance A is a protein, examples of the analogue may include those analogues in which some amino acids of the protein are deleted or some amino acids are added to the structure of the protein, and which are capable of undergoing specific binding reaction with the specific binding partner.

As used herein, the "analogue" in "substance B or an analogue thereof" is not particularly limited so long as it is a substance capable of undergoing specific binding reaction with a specific binding partner for substance B and it is a substance other than substance B. The analogue is, in general, similar to substance B in structure. When substance B is a protein, examples of the analogue may include those analogues in which some amino acids of the protein are deleted or some amino acids are added to the structure of the protein, and which are capable of undergoing specific binding reaction with the specific binding partner.

As used herein, the specific binding reaction is an antigen-antibody reaction when the specific binding partner is an antibody, but may otherwise be exemplified by the avidin-biotin binding reaction and hormone-hormone receptor binding reactions.

As used herein, the fine particles are those fine particles that are commonly used for immune agglutination reaction in the field of clinical testing, and they may be used just as they are. The most common fine particles are latex particles. Fine particles of, for example, 10 to 500 nm in diameter are used.

In the present invention, when a substance or its analogue is carried on fine particles, known conventional methods of carrying such as a physical adsorption by a hydrophobic interaction and a covalent binding can be used.

In the present invention, as a method of measuring the degree of agglutination, it is usually preferable to measure the generated turbidity by absorbance, preferably at any wavelength from 340 to 940 nm. As a method of measuring the degree of agglutination, it is also possible to perform macroscopic observation of the aggregates or counting the number of non-agglutinated fine particles, thereby enabling the assay of the level of a substance in a sample.

As used herein, the automatic analyzer is not limited as long as it is an apparatus that can measure a component in a sample based on the degree of its agglutination in a homogeneous system by automatically adding at least one or more liquid reagents to the sample, and it is preferably a general-purpose automatic biochemical analyzer that is used in the field of clinical testing. Examples of such apparatuses may include, for example, Hitachi type 7180 automatic analyzer, type 7170S automatic analyzer, type 7600 automatic analyzer, JEOL type BM2250 automatic analyzer, Toshiba type TBA-200FR automatic analyzer, Olympus type AU640 automatic analyzer, and BECKMAN COULTER IMMAGE800.

In the present invention, to assay the level of complex AB in a sample, a kit for assaying the level of complex AB in a sample comprising, for example, i) a reagent containing fine particles carrying substance A or its analogue and substance B or its analogue, ii-A) a reagent containing the substance A-specific binding partner C, ii-B) a reagent containing the substance B-specific binding partner D, and ii-C) a reagent containing the substance A-specific binding partner C and the substance B-specific binding partner D can be used.

To carry out the method of the present invention to assay complex AB, both of substance A and substance B are preferably proteins from the point that antibodies can be used as specific binding partners. As a specific method in this case, a method of assaying IgA-albumin complex using three kinds of competitive homogeneous turbidimetric immunoassay will be described in more detail as an example (in this case, if substance A and substance B are both proteins, the explanation will be more generalized by substituting substance A and substance B for IgA and albumin, respectively, in the followings).

i) A Reagent Containing Latex Particles Sensitized with IgA and Albumin (a Reagent Containing Fine Particles Carrying Substance A or its Analogue and Substance B or its Analogue):

A 1-mL solution of 1-ethyl-3-(3-dimethylaminopropyl)-carbodiimide (EDC) dissolved in a buffer is added to a 3-20% solution of latex particles having carboxyl groups on the surface and a particle diameter of 10 to 500 nm to prepare an EDC-containing latex solution.

Subsequently, an IgA solution is added to the EDC-containing latex solution, and then the carboxyl group of the latex particles and the amino group of IgA are bound through a condensation reaction by stirring at 0 to 40° C. for 5 minutes to 10 hours, followed by addition of albumin solution to stop the reaction. Then, centrifugation at 3,000 to 30,000 rpm is performed, and the supernatant is discarded to recover the precipitate. This precipitate is suspended in an albumin solution and dispersed completely by ultrasonic treatment, followed by stirring at 0 to 40° C. Then, 3,000 to 30,000 rpm centrifugation is performed, and the obtained precipitate is suspended in a buffer solution and dispersed completely by ultrasonic treatment to obtain the latex particles sensitized with IgA and albumin, which is used as the first reagent after a dilution with a buffer.

ii-A) A Reagent Containing Anti-IgA Antibody (a Reagent Containing the Substance-A Specific Binding Partner C):

A buffer solution is added to anti-IgA antibody such as goat anti-human IgA serum to obtain a solution of a reagent containing anti-IgA antibody, which is used as the second reagent-A. This anti-IgA antibody is capable of undergoing specific binding reaction with both of IgA present in IgA-albumin complex and IgA present in a free form.

ii-B) A Reagent Containing Anti-Albumin Antibody (a Reagent Containing the Substance-B Specific Binding Partner D):

A buffer solution is added to anti-albumin antibody such as goat anti-human albumin serum γ-fraction to obtain a solution of a reagent containing anti-albumin antibody, which is used as the second reagent-B. This anti-albumin antibody is capable of undergoing specific binding reaction with both of albumin present in IgA-albumin complex and albumin present in a free form.

ii-C) A Reagent Containing Anti-IgA Antibody and Anti-Albumin Antibody (a Reagent Containing the Substance A-Specific Binding Partner C and the Substance B-Specific Binding Partner D):

The above mentioned anti-IgA antibody such as goat anti-human IgA serum and anti-albumin antibody such as goat anti-human albumin serum γ-fraction are diluted in a buffer solution to obtain a reagent containing anti-IgA antibody and anti-albumin antibody such as a mixed antiserum solution, which is used as the second reagent-C.

Measurement of IgA-Albumin Complex:

For the measurement of IgA-albumin complex, using a general-purpose automatic biochemical analyzer such as Hitachi type 7180, 50 to 200 μL of the first reagent and 50 to 200 μL of the second reagent (any one of -A, -B, and -C) are reacted with 2 to 20 μL of a sample, and the change of absorbance level between the photometric points of, for example, 16 and 34 (corresponding to five minutes just after the addition of the second reagent) is measured at a wavelength of 340 to 800 nm by a two-point end method.

If the sample is reacted with a combination of the first reagent and the second reagent-A (anti-IgA antibody), the level of IgA present in IgA-albumin complex and in a free form in the sample (value P) can be measured by a competitive homogeneous agglutination assay. If the sample is reacted with a combination of the first reagent and the second reagent-B (anti-albumin antibody), the level of albumin present in IgA-albumin complex and in a free form in the sample (value Q) can be measured by a competitive homogeneous immunoagglutination assay. If the sample is reacted with a combination of the first reagent and the second reagent-C (anti-IgA antibody and anti-albumin antibody), value R can be obtained by a competitive homogeneous immunoagglutination assay.

The units of values P, Q and R are not restricted provided that they are in an identical unit, and they may be, for example, the amount of absorbance change itself, or otherwise units of concentration by weight such as mg/dL and molar concentration such as mmol/L calculated with reference to a calibration curve may be used. From these values, P+Q−R is obtained as value α, which is the level of IgA-albumin complex.

Further, IgA-albumin complex may most preferably be measured using three kinds of competitive homogeneous turbidimetric immunoassays as described above, but IgA-albumin complex in a sample may otherwise be determined, for example, by an immunoassay using an antibody against IgA and an antibody against albumin. For example, the complex can be measured by a method in which the complex in a sample is determined by allowing the complex to get contact with a solid phase antibody made through binding either one of an antibody against IgA and an antibody against albumin to a solid phase, and simultaneously to react with a labeled antibody derived from the other antibody that is not immobilized to the solid phase. By means of the methods like these, the presence of IgA-type M-proteinemia may be determined through the measurement of the level of IgA-albumin complex.

Hereinafter, the present invention will be described in more detail with reference to Examples. The invention, however, should not be limited to these Examples.

EXAMPLE 1

Measurement of Human Serum Levels of IgA-Albumin Complex

1) Preparation of Latex Particles Sensitized with Human IgA and Human Albumin (Hereinafter, in Some Cases, Referred to as IgA/Albumin-Sensitized Latex Particles)

The binding of human IgA and human albumin to latex particles was performed as follows.

To 8.5 mL of a solution of latex particles having carboxyl groups on the surface and a particle diameter of 108 nm set at a concentration of 11.76% by 2-morpholinoethanesulfonic acid monohydrate (MES) buffer solution, 1 mL of a solution of 1-ethyl-3-(3-dimethylaminopropyl)-carbodiimide (EDC) adjusted to 400 mg/mL with a MES buffer solution was added to prepare an EDC-containing latex solution.

Then, apart from this, human IgA crudely purified from normal human serum (33 mg/mL) was diluted to a concentration of 0.3 mg/mL with tris(hydroxymethyl)aminomethane (Tris) buffer solution-1. 100 mL of this solution was added to the EDC-containing latex solution, and the carboxyl group of the latex particles and the amino group of IgA were bound through a condensation reaction by stirring at room temperature for an hour, followed by addition of 50 mL of human albumin solution to stop the reaction. Then, centrifugation at 20,000 rpm was performed for an hour, and the supernatant is discarded to recover the precipitate. This precipitate was suspended in 50 mL of human albumin solution and dispersed completely by ultrasonic treatment, followed by stirring at room temperature for an hour. Then, centrifugation at 20,000 rpm was performed, and the obtained precipitate was suspended in 100 mL of Tris buffer solution-2 and dispersed completely by ultrasonic treatment to obtain the IgA/albumin-sensitized latex particles of 1% concentration.

2) Preparation of the First Reagent for the Measurement of Human IgA-Albumin Complex The first reagent was prepared using the IgA/albumin-sensitized latex particles.

The first reagent for use was prepared as a 0.1% latex solution by adding 90 mL of Tris buffer-2 to 10 mL of the IgA/albumin-sensitized latex particles of 1% concentration.

3) Preparation of the Second Reagent for the Measurement of Human IgA-Albumin Complex Three kinds of second reagents were prepared using goat anti-human IgA serum, goat anti-human albumin serum γ-fraction, and a mixture of these two sera.

The second reagent-A (anti-IgA antibody) for use was prepared as a 0.15% solution of goat anti-human IgA serum by adding 99.85 mL of Tris buffer-2 to 0.15 mL of goat anti-human IgA serum.

The second reagent-B (anti-albumin antibody) for use was prepared as a 1.1% solution of goat anti-human albumin serum γ-fraction by adding 98.9 mL of Tris buffer-2 to 1.1 mL of goat anti-human albumin serum γ-fraction.

The second reagent-C (anti-IgA antibody and anti-albumin antibody) for use was prepared as a mixed antiserum solution of 0.15% goat anti-human IgA serum and 1.1% goat anti-human albumin serum γ-fraction by adding 98.75 mL of Tris buffer-2 to a mixture of 0.15 mL of goat anti-human IgA serum and 1.1 mL of goat anti-human albumin serum γ-fraction.

For these three kinds of second reagents prepared, as the respective first reagents, the latex solution described above was used in common.

If the sample is reacted with a combination of the first reagent and the second reagent-A (anti-IgA antibody), the level of IgA in the sample (value P) can be measured by a competitive homogeneous agglutination assay. If the sample is reacted with a combination of the first reagent and the second reagent-B (anti-albumin antibody), the level of albumin in the sample (value Q) can be measured by a competitive homogeneous immunoagglutination assay. If the sample is reacted with a combination of the first reagent and the second reagent-C (anti-IgA antibody and anti-albumin antibody), value R can be obtained by a competitive homogeneous immunoagglutination assay.

The composition of each reagent is as follows.

Tris buffer-1

| Tris | 50 mM | pH 7.4 |
|---|---|---|
| NaCl | 100 mM | |

Human albumin solution

| Tris | 12.4 mM | pH 7.5 |
|---|---|---|
| Urea | 20 mM | |
| Human albumin (SCRIPPS, Inc.) | 10% | |

Human albumin (SCRIPPS, Inc.) 10%
Tris buffer-2

| Tris | 50 mM | pH 7.4 |
|---|---|---|
| NaCl | 100 mM | |
| Triton-X100 ™ | 0.1% | |

(t-octylphenoxypolyethoxyethanol)

4) Preparation of a Calibration Curve

As a standard sample, a serum with known concentrations of human IgA and human albumin was used at an appropriate dilution with Tris buffer-2. The concentration of a standard sample for the second reagent-C was defined as the sum of known concentrations of IgA and albumin in a single serum.

For the measurement of human IgA/albumin complex, using an automatic analyzer Hitachi type 7180, 120 μL of the first reagent and 120 μL of the second reagent (any one of -A, -B, and -C) were reacted with 12 μL of a sample, and the change of absorbance level between the photometric points of 16 and 34 (corresponding to five minutes just after the addition of the second reagent) was measured at a wavelength of 570 nm by a two-point end method.

Figure 2:
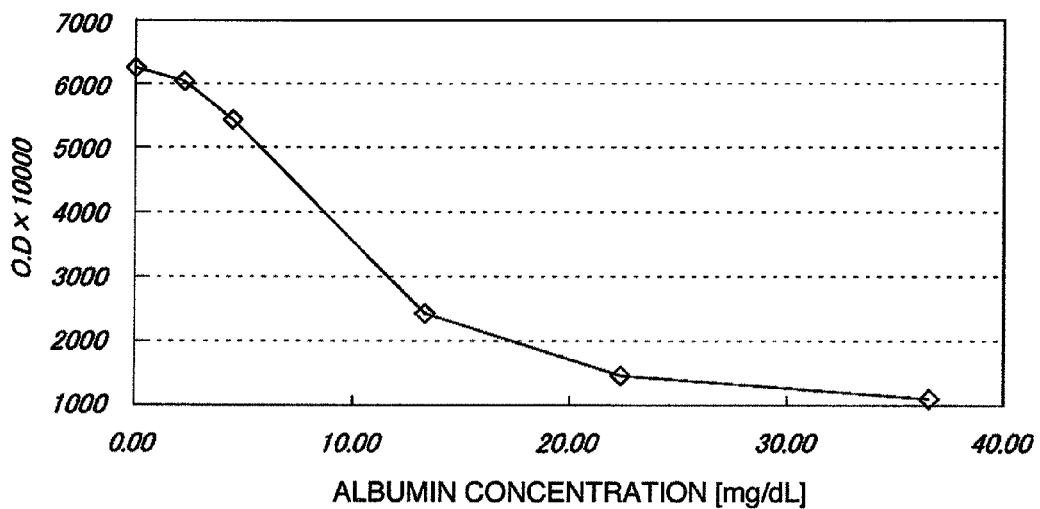
FIG. 2 shows the change of absorbance level when a standard sample was measured using a first reagent and a second reagent-B in Example 1.
Figure 3:
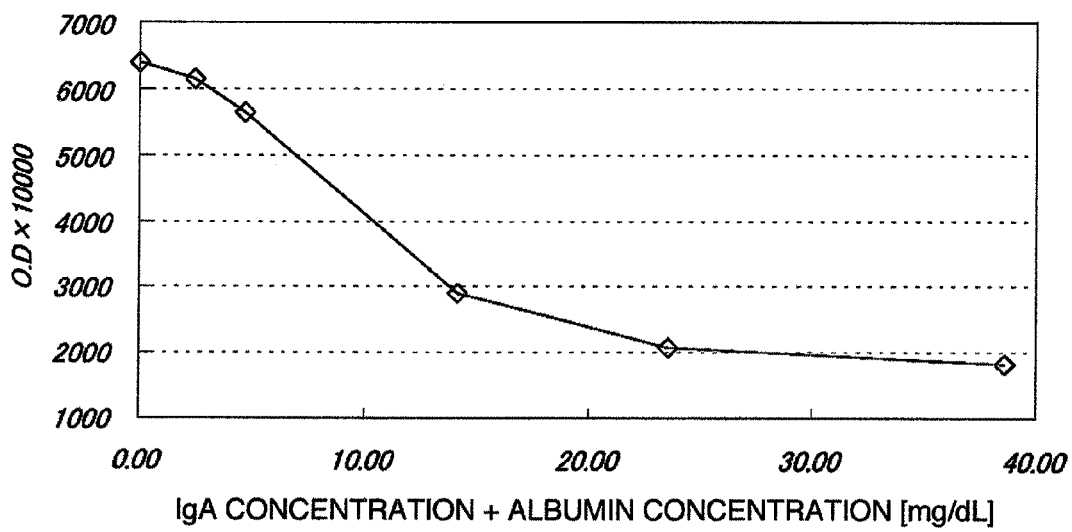
FIG. 3 shows the change of absorbance level when a standard sample was measured using a first reagent and a second reagent-C in Example 1.

Changes in absorbance when measurements were performed on a standard sample using the first reagent in common and the second reagent-A, -B, or -C are shown, respectively, in Table 1, 2 or 3 and FIG. 1, 2 or 3.

TABLE 1

Amount of change in absorbance when a measurement was performed on a standard sample using the second reagent-A (anti-IgA antibody)

| Serum IgA concentration (mg/dL) | Amount of change in absorbance (OD × 10000) Main-wavelength 570 nm, Sub-wavelength 800 nm |
|---|---|
| 0.00 | 3406 |
| 0.13 | 3277 |
| 0.25 | 3148 |
| 0.74 | 2704 |
| 1.27 | 2322 |
| 2.08 | 1855 |

TABLE 2

Amount of change in absorbance when a measurement was performed on a standard sample using the second reagent-B (anti-albumin antibody)

| Serum albumin concentration (mg/dL) | Amount of change in absorbance (OD × 10000) Main-wavelength 570 nm, Sub-wavelength 800 nm |
|---|---|
| 0.00 | 6254 |
| 2.27 | 6019 |
| 4.47 | 5445 |
| 13.42 | 2433 |
| 22.30 | 1451 |
| 36.56 | 1115 |

TABLE 3

Amount of change in absorbance when a measurement was performed on a standard sample using the second reagent-C (anti-IgA antibody and anti-albumin antibody)

| Serum IgA concentration + Serum albumin concentration (mg/dL) | Amount of change in absorbance (OD × 10000) Main-wavelength 570 nm, Sub-wavelength 800 nm |
|---|---|
| 0.00 | 6400 |
| 2.40 | 6151 |
| 4.72 | 5626 |
| 14.16 | 2905 |
| 23.57 | 2080 |
| 38.64 | 1835 |

As shown in Tables 1 to 3 and FIGS. 1 to 3, with the increase of the amounts of human IgA and human albumin in the standard solution, the change of absorbance level was decreased by a competitive reaction in any of the reagents used.

This shows that the values of IgA, albumin and R can also be determined in concentration by measuring the respective changes in absorbance with combinations of the first reagent and the second reagent-A, -B, or -C.

5) Confirmation of IgA and Albumin Measurements Using the Second Reagents-A and -B To confirm if it is possible to measure IgA and albumin in a sample accurately using the second reagents-A and -B, the presence or absence of a correlation between these reagents and the reagents for the measurements of serum IgA and serum albumin by turbidimetric immunoassay (TIA method) was examined.

A serum confirmed not to contain IgA-albumin complex by Western Blot method was appropriately diluted with Tris buffer-2 for use as a sample. Measurements were calculated with reference to a calibration curve produced by the multi-point calibration curve generating function of Hitachi 7180 type automatic analyzer with the use of the standard sample mentioned above. The first reagent and the second reagents-A and -B of the present invention were used as assay reagents, and commercially available reagents for the TIA method, namely, "N-assay TIA IgA-RC" and "N-assay TIA Micro Alb" (produced by Nitto Boseki Co., Ltd.) were used as control reagents.

As measurement parameters for the reagents of the present invention the aforementioned criteria were used, and for the TIA methods the specified parameters and the standard solution were used.

Figure 4:
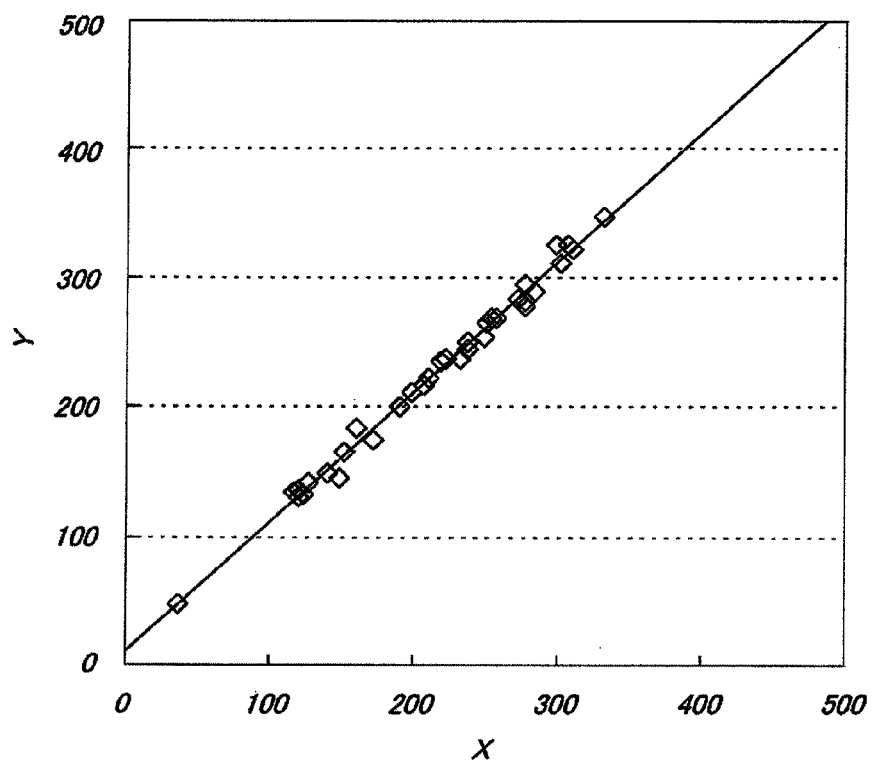
FIG. 4 shows the correlation of IgA measurements of samples between the result obtained using the first reagent and the second reagent-A and that obtained using a conventional turbidimetric immunoassay (TIA method) in Example 1.
Figure 5:
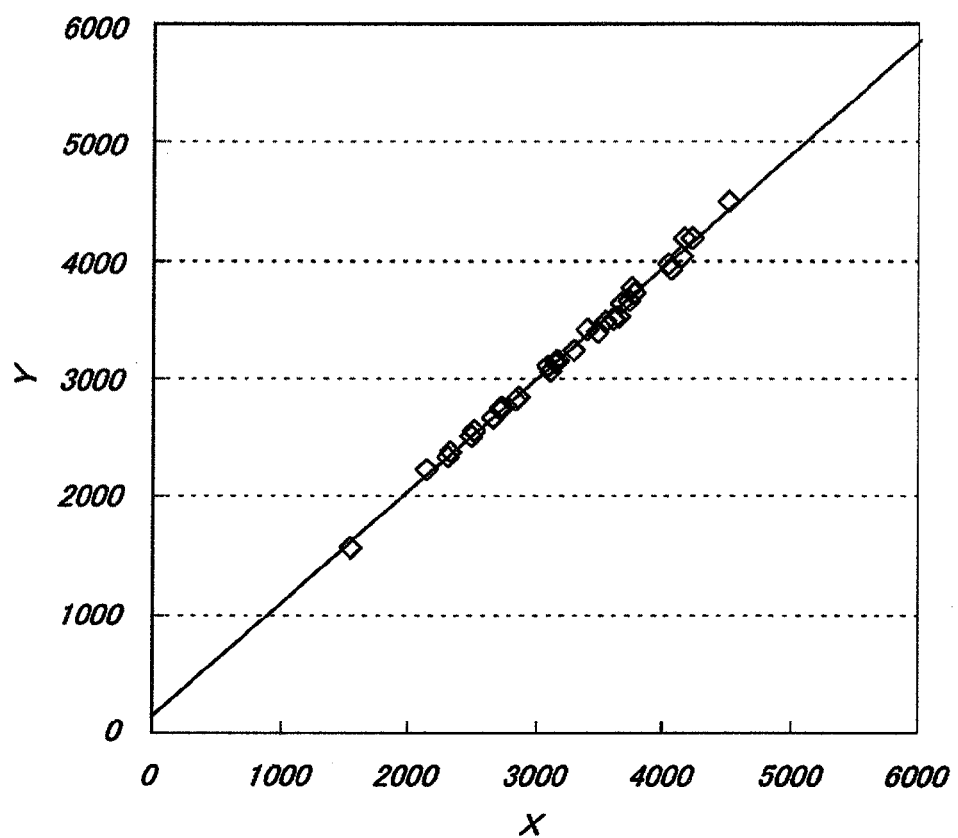
FIG. 5 shows the correlation of albumin measurements of samples between the result obtained using the first reagent and the second reagent-B and that obtained using a conventional turbidimetric immunoassay (TIA method) in Example 1.

The results on correlation with the reagents of the present invention are shown in FIGS. 4 and 5. The measurements, however, were performed on the samples appropriately diluted, and hence values multiplied by the dilution ratio are shown.

As shown in FIGS. 4 and 5, the confirmation of correlation by designating the TIA method as X and the reagent of the present invention as Y gave favorable results for both the second reagent-A and the second reagent-B, that is, Y=1.006X+10.65 and a correlation coefficient of 0.9962 for the second reagent-A, and Y=0.9481X+144.9 and a correlation coefficient of 0.9981 for the second reagent-B. Since the correlation with TIA method has been confirmed, it can be said that serum IgA and serum albumin are both to be accurately measured by using the second reagents-A and -B.

6) Levels of IgA-Albumin Complex in Human Serum

Measurements were performed using the first reagent and the second reagents-A, -B and -C under the same conditions as described above.

In addition to the foregoing sample, a serum confirmed to contain IgA-albumin complex by Western Blot method was also used after an appropriate dilution with Tris buffer-2.

Figure 6:
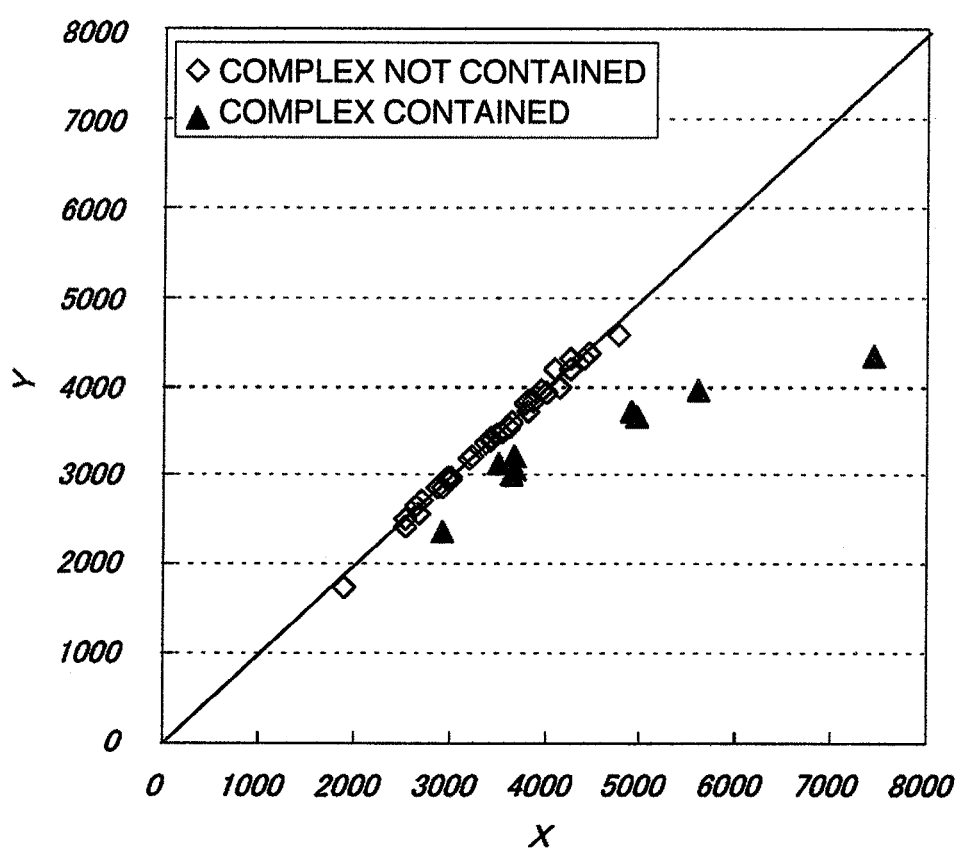
FIG. 6 shows the correlation between [the value calculated by the use of the second reagent-A+the value calculated by the use of the second reagent-B] (X) and [the value calculated by the use of the second reagent-C] (Y) with regard to serum samples not containing IgA-albumin complex and test samples containing IgA-albumin complex in Example 1.
Figure 7:
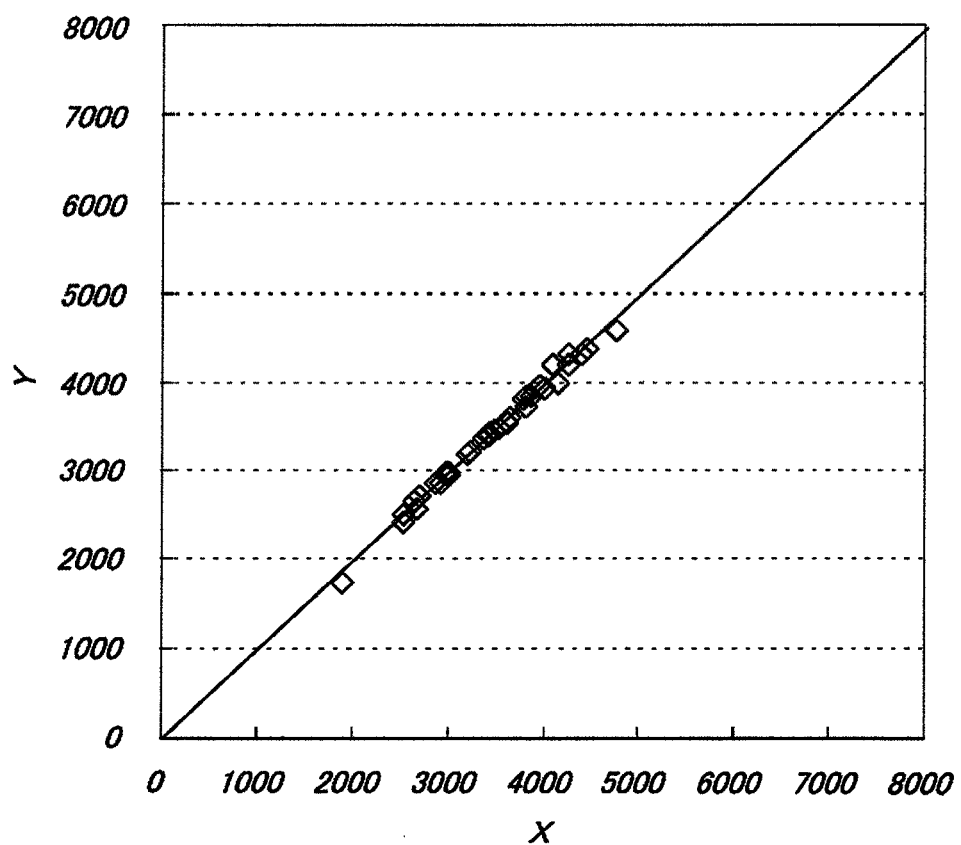
FIG. 7 shows the correlation between [the value calculated by the use of the second reagent-A+the value calculated by the use of the second reagent-B] (X) and [the value calculated by the use of the second reagent-C] (Y) with regard to serum samples not containing IgA-albumin complex in Example 1.

With respect to the reagents of the present invention, the correlation between [the value calculated by the use of the second reagent-A+the value calculated by the use of the second reagent-B] (X) and [the value calculated by the use of the second reagent-C] (Y) is shown in FIGS. 6 and 7.

FIG. 6 shows the result obtained with all the test samples involving sera not containing IgA-albumin complex and sera containing IgA-albumin complex, and FIG. 7 shows a correlation diagram with regard only to sera not containing IgA-albumin complex.

Confirmation of correlation gave a favorable result with regard only to sera not containing IgA-albumin complex (FIG. 7), that is, Y=0.9962X−29.91 and a correlation coefficient of 0.9963. As shown in FIG. 6, however, the result of sera containing IgA-albumin complex showed a great deviation from the correlation equation obtained with sera not containing IgA-albumin complex. This is a tendency observed specifically in sera containing IgA-albumin complex.

Here, if [the value calculated by the use of the second reagent-A], that is the level of IgA, is designated as level P, [the value calculated by the use of the second reagent-B], that is the level of albumin, as level Q, and [the value calculated by the use of the second reagent-C] as R, the relationship: α=P+Q−R≈0 is established in case IgA-albumin complex is not contained. On the other hand, in case IgA-albumin complex is contained, the relationship: α=P+Q−R>0 is established. As shown in Table 4, from the results of actual measurement of sera, the α of test samples containing the complex is significantly higher than the a of test samples not containing the complex, and thus it can be proven that this relationship is established.

TABLE 4

| Sample | P + Q (mg/dL) | R (mg/dL) | α |
| --- | --- | --- | --- |
| Not containing: 1 | 3544 | 3496 | 48 |
| Not containing: 2 | 3814 | 3832 | −18 |
| Not containing: 3 | 4454 | 4380 | 74 |
| Not containing: 4 | 4254 | 4180 | 74 |
| Not containing: 5 | 4092 | 4184 | −92 |
| Containing: 1 | 3641 | 3014 | 627 |
| Containing: 2 | 3680 | 3205 | 475 |
| Containing: 3 | 2928 | 2354 | 574 |
| Containing: 4 | 7439 | 4325 | 3114 |
| Containing: 5 | 4897 | 3721 | 1176 |
| Containing: 6 | 4959 | 3651 | 1308 |
| Containing: 7 | 5595 | 3941 | 1654 |
| Containing: 8 | 3518 | 3122 | 396 |
| Containing: 9 | 3671 | 3073 | 598 |

Therefore, from the above-mentioned, it has been proven that the reagents of the present invention are capable of measuring the level of IgA-albumin complex in human serum in a comprehensive and specific manner by using the first reagent in common and three kinds of the second reagents. In addition, it has been proven that patients with IgA-type M-proteinemia can be diagnosed by determining the level of IgA-albumin complex.

INDUSTRIAL APPLICABILITY

The assay method and the kit of the present invention for the measurement of complexes by a competitive homogeneous agglutination assay make it possible to measure the level of a complex like IgA-albumin complex in a sample easily using readily available reagents. In addition, this method and kit can be applied to general-purpose automatic biochemical analyzer, and thus a complex of interest can be assayed easily in multiple samples in a short time.

The invention claimed is:

1. A method of assaying the level of complex AB of substance A and substance B in a sample which is likely to contain complex AB, comprising:
   i) determining level P, which is the level of substance A present in complex AB and in a free form in the sample, through the steps of mixing the sample, a substance A-specific binding partner C, and fine particles carrying both substance A or an analogue thereof and substance B or an analogue thereof, in order to allow competition for a specific binding reaction with the specific binding partner C between substance A present in complex AB and in a free form in the sample and substance A or the analogue carried on the fine particles; measuring the degree of agglutination of said fine particles via the specific binding partner C; and determining level P based on the degree of agglutination of said fine particles via the specific binding partner C;
   ii) determining level Q, which is the level of substance B present in complex AB and in a free form in the sample, through the steps of: mixing the sample, a substance B-specific binding partner D, and the fine particles carrying both substance A or the analogue and substance B or the analogue, in order to allow competition for a specific binding reaction with the specific binding partner D between substance B present in complex AB and in a free form in the sample and substance B or the analogue carried on the fine particles; measuring the degree of agglutination of said fine particles via the specific binding partner D; and determining level Q based on the degree of agglutination of said fine particles via the specific binding partner D;
   iii) determining level R through the steps of; mixing the sample, the substance A-specific binding partner C, the substance B-specific binding partner D, and the fine particles carrying both substance A or the analogue and substance B or the analogue, in order to allow competition for a specific binding reaction with the specific binding partner C between substance A present in complex AB and in a free form in the sample and substance A or the analogue carried on the fine particles as well as competition for a specific binding reaction with the specific binding partner D between substance B present in complex AB and in a free form in the sample and substance B or the analogue carried on the fine particles; measuring the degree of agglutination of said fine particles via the specific binding partners C and D; and determining level R based on the degree of agglutination of said fine particles via the specific binding partners C and D; and
   iv) calculating level a of complex AB according to the formula α=P+Q−R;
   wherein said substance A-specific binding partner C is an anti-A antibody; and wherein said substance B-Specific binding partner D is an anti-B antibody.

2. The method according to claim 1, wherein substance A and substance B are proteins.

3. The method according to claim 1, wherein the fine particles are latex particles.

4. The method according to claim 3, wherein the degree of agglutination are determined through absorbance at any wavelength of from 340 to 940 nm.

5. The method according to claim 1, wherein the sample is a biological sample.

6. The method according to claim 1, wherein substance A, substance B, the specific binding partner C, the specific binding partner D, and complex AB are IgA, albumin, an anti-IgA antibody, an anti-albumin antibody, and IgA-albumin complex, respectively, and the specific binding reaction is an antigen-antibody reaction.

7. A method of assaying the level of complex AB of substance A and substance B in a sample which is likely to contain complex AB, by comprising:
   i) determining level P, which is the level of substance A present in complex AB and in a free form in the sample;
   ii) determining level Q, which is the level of substance B present in complex AB and in a free form in the sample; and iii) determining level R through the steps of mixing the sample, a substance A-specific binding partner C, a substance B-specific binding partner D, and fine particles carrying both substance A or an analogue thereof and substance B or an analogue thereof in order to allow competition for a specific binding reaction with the specific binding partner C between substance A present in complex AB and in a free form in the sample and substance A or the analogue carried on the fine particles as well as competition for a specific binding reaction with the specific binding partner D between substance B present in complex AB and in a free form in the sample and substance B or the analogue carried on the fine particles; measuring the degree of agglutination of said fine particles via the specific binding partners C and D; and determining level R based on the degree of agglutination of said fine particles via the specific binding partners C and D; and iv) calculating level $\alpha$ of complex AB according to the formula $\alpha = P + Q - R$;

wherein said substance A-specific binding partner C is an anti-A antibody; and wherein said substance B-specific binding partner D is an anti-B antibody.

* * * * *